United States Patent [19]
Houghten et al.

[11] Patent Number: 5,578,573
[45] Date of Patent: Nov. 26, 1996

[54] VIRAL INTEGRASE INHIBITING PEPTIDES

[75] Inventors: Richard A. Houghten, Del Mar; Patricia A. Weber, San Diego, both of Calif.; Ronald H. A. Plasterk, Bussum; Ramon A. Puras Lutzke, Amsterdam, both of Netherlands

[73] Assignee: Houghten Pharmaceuticals, Inc., San Diego, Calif.

[21] Appl. No.: 375,911

[22] Filed: Jan. 20, 1995

[51] Int. Cl.$^6$ ............ A61K 38/08; C07K 7/06; C12N 9/12

[52] U.S. Cl. ............ 514/17; 435/194; 530/329

[58] Field of Search ............ 530/329; 514/17; 435/194

[56] References Cited

U.S. PATENT DOCUMENTS 5,141,735  8/1992  Bellemin et al. ............ 424/85.1
5,413,914  5/1995  Franzusoff ............ 435/224

OTHER PUBLICATIONS

Neuzil, Kathleen Maletic, "Pharmacologic Therapy for Human Immunodeficiency Virus Infection: A Review." *Amer. J. Med. Sci.* 307:368–373 (1994).

Cushman and Sherman, "Inhibition of HIV–1 Integration Protein by Aurintricarboxylic Acid Monomers, Monomer Analogs, and Polymer Fractions." *Biomed. Biophy. Res. Comm.* 185:85–90 (1992).

Fesen, Mark R. et al., "Inhibitors of Human Immunodeficiency Virus Integrase." *Proc. Natl. Acad. Sci. USA* 90:2399–2403 (1993).

Fesen, Mark R. et al., "Inhibition of HIV–1 Integrase by Flavones, Caffeic Acid Phenethly Ester (CAPE) and Related Compounds." *Biomed. Pharm.* 48:595–608 (1994).

Lafemina, Robert L. et al., "Inhibition of Human Immunodeficiency Virus Integrase by Bis–Chatechols." *Antimicr. Agents. and Chemother.* 39:320–324 (1995).

Mazumder, Abhijit et al., "Inhibition of Human Immunodeficiency Virus Type 1 Integrase by 3'–azido–3'–deoxythymidylate." *Proc. Natl. Acad. Sci. USA* 91:5771–5775 (1994).

Mazumder, Abhijit et al., "Inhibition of Human Immunodeficiency Virus Type 1 Integrase by a Hydrophobic Cation: The Phenanthroline–Cuprous Complex." *Aids Res. and Human Retro.* 11:115–125 (1995).

*Primary Examiner*—Jeffrey E. Russel
*Attorney, Agent, or Firm*—Campbell & Flores

[57] ABSTRACT

The present invention provides viral integrase inhibiting peptides having the general structure,

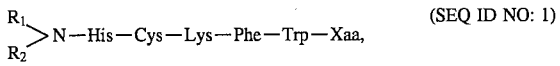

(SEQ ID NO: 1)

where Xaa is an amino acid or an amino acid analog, the stereochemistry of the amino acids or amino acid analogs can be D-amino acids or L-amino acids and the amino and carboxy termini of the peptide can be modified. The invention also provides viral inhibiting peptides having essentially the amino acid sequence,

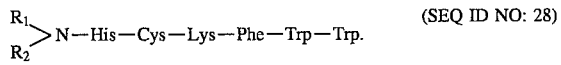

(SEQ ID NO: 28)

The invention also provides a pharmaceutical composition comprising a viral integrase inhibiting peptide and methods of using a viral integrase inhibiting peptide in vitro or in vivo to reduce or inhibit viral integrase activity in a cell and the infectivity of a virus.

42 Claims, No Drawings

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
 ( A ) LENGTH: 6 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:1:

```
His  Cys  Lys  Phe  Trp  Xaa
1                   5
```

( 2 ) INFORMATION FOR SEQ ID NO:2:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 6
  ( D ) OTHER INFORMATION: /note="PEPTIDE IS AMIDATED AT CARBOXY TERMINUS"

( x i ) SEQUENCE DESCRIPTION: SEQ ID NO:2:

```
His  Cys  Lys  Phe  Trp  Ala
1                   5
```

( 2 ) INFORMATION FOR SEQ ID NO:3:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 6
  ( D ) OTHER INFORMATION: /note="PEPTIDE IS AMIDATED AT CARBOXY TERMINUS"

( x i ) SEQUENCE DESCRIPTION: SEQ ID NO:3:

```
His  Cys  Lys  Phe  Trp  Arg
1                   5
```

( 2 ) INFORMATION FOR SEQ ID NO:4:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 6
  ( D ) OTHER INFORMATION: /note="PEPTIDE IS AMIDATED AT CARBOXY TERMINUS"

( x i ) SEQUENCE DESCRIPTION: SEQ ID NO:4:

```
His  Cys  Lys  Phe  Trp  Asn
1                   5
```

( 2 ) INFORMATION FOR SEQ ID NO:5:

( i ) SEQUENCE CHARACTERISTICS:
　　　　( A ) LENGTH: 6 amino acids
　　　　( B ) TYPE: amino acid
　　　　( C ) STRANDEDNESS: single
　　　　( D ) TOPOLOGY: linear ( i i ) MOLECULE TYPE: peptide ( i x ) FEATURE:
　　　　( A ) NAME/KEY: Peptide
　　　　( B ) LOCATION: 6
　　　　( D ) OTHER INFORMATION: /note="PEPTIDE IS AMIDATED AT
　　　　　　CARBOXY TERMINUS"'

( x i ) SEQUENCE DESCRIPTION: SEQ ID NO:5:

His　Cys　Lys　Phe　Trp　Asp
　　1　　　　　　　　　　　5

( 2 ) INFORMATION FOR SEQ ID NO:6:

( i ) SEQUENCE CHARACTERISTICS:
　　　　( A ) LENGTH: 6 amino acids
　　　　( B ) TYPE: amino acid
　　　　( C ) STRANDEDNESS: single
　　　　( D ) TOPOLOGY: linear ( i i ) MOLECULE TYPE: peptide ( i x ) FEATURE:
　　　　( A ) NAME/KEY: Peptide
　　　　( B ) LOCATION: 6
　　　　( D ) OTHER INFORMATION: /note="PEPTIDE IS AMIDATED AT
　　　　　　CARBOXY TERMINUS"

( x i ) SEQUENCE DESCRIPTION: SEQ ID NO:6:

His　Cys　Lys　Phe　Trp　Cys
　　1　　　　　　　　　　　5

( 2 ) INFORMATION FOR SEQ ID NO:7:

( i ) SEQUENCE CHARACTERISTICS:
　　　　( A ) LENGTH: 6 amino acids
　　　　( B ) TYPE: amino acid
　　　　( C ) STRANDEDNESS: single
　　　　( D ) TOPOLOGY: linear ( i i ) MOLECULE TYPE: peptide ( i x ) FEATURE:
　　　　( A ) NAME/KEY: Peptide
　　　　( B ) LOCATION: 6
　　　　( D ) OTHER INFORMATION: /note="PEPTIDE IS AMIDATED AT
　　　　　　CARBOXY TERMINUS"

( x i ) SEQUENCE DESCRIPTION: SEQ ID NO:7:

His　Cys　Lys　Phe　Trp　Glu
　　1　　　　　　　　　　　5

( 2 ) INFORMATION FOR SEQ ID NO:8:

( i ) SEQUENCE CHARACTERISTICS:
　　　　( A ) LENGTH: 6 amino acids
　　　　( B ) TYPE: amino acid
　　　　( C ) STRANDEDNESS: single
　　　　( D ) TOPOLOGY: linear ( i i ) MOLECULE TYPE: peptide ( i x ) FEATURE:
　　　　( A ) NAME/KEY: Peptide
　　　　( B ) LOCATION: 6
　　　　( D ) OTHER INFORMATION: /note="PEPTIDE IS AMIDATED AT

CARBOXY TERMINUS"

( x i ) SEQUENCE DESCRIPTION: SEQ ID NO:8:

```
His  Cys  Lys  Phe  Trp  Gln
1                   5
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT
            CARBOXY TERMINUS"

( x i ) SEQUENCE DESCRIPTION: SEQ ID NO:9:

```
His  Cys  Lys  Phe  Trp  Gly
1                   5
```

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT
            CARBOXY TERMINUS"

( x i ) SEQUENCE DESCRIPTION: SEQ ID NO:10:

```
His  Cys  Lys  Phe  Trp  His
1                   5
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT
            CARBOXY TERMINUS"

( x i ) SEQUENCE DESCRIPTION: SEQ ID NO:11:

```
His  Cys  Lys  Phe  Trp  Ile
1                   5
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single (D) TOPOLOGY: linear (ii) MOLECULE TYPE: peptide (ix) FEATURE:
    (A) NAME/KEY: Peptide
    (B) LOCATION: 6
    (D) OTHER INFORMATION: /note="PEPTIDE IS AMIDATED AT CARBOXY TERMINUS"

(xi) SEQUENCE DESCRIPTION: SEQ ID NO:12:

His Cys Lys Phe Trp Leu
1                   5

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 6
        (D) OTHER INFORMATION: /note="PEPTIDE IS AMIDATED AT CARBOXY TERMINUS"

(xi) SEQUENCE DESCRIPTION: SEQ ID NO:13:

His Cys Lys Phe Trp Lys
1                   5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
       (B) LOCATION: 6
        (D) OTHER INFORMATION: /note="PEPTIDE IS AMIDATED AT CARBOXY TERMINUS"

(xi) SEQUENCE DESCRIPTION: SEQ ID NO:14:

His Cys Lys Phe Trp Met
1                   5

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 6
        (D) OTHER INFORMATION: /note="PEPTIDE IS AMIDATED AT CARBOXY TERMINUS"

(xi) SEQUENCE DESCRIPTION: SEQ ID NO:15:

His Cys Lys Phe Trp Phe
1                   5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT
            CARBOXY TERMINUS"

( x i ) SEQUENCE DESCRIPTION: SEQ ID NO:16:

His  Cys  Lys  Phe  Trp  Pro
1                          5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT
            CARBOXY TERMINUS"

( x i ) SEQUENCE DESCRIPTION: SEQ ID NO:17:

His  Cys  Lys  Phe  Trp  Ser
1                          5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT
            CARBOXY TERMINUS"

( x i ) SEQUENCE DESCRIPTION: SEQ ID NO:18:

His  Cys  Lys  Phe  Trp  Thr
1                          5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide (B) LOCATION: 6
(D) OTHER INFORMATION: /note="PEPTIDE IS AMIDATED AT CARBOXY TERMINUS"

(x i) SEQUENCE DESCRIPTION: SEQ ID NO:19:

His Cys Lys Phe Trp Trp
1               5

(2) INFORMATION FOR SEQ ID NO:20:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i x) FEATURE:
(A) NAME/KEY: Peptide
(B) LOCATION: 6
(D) OTHER INFORMATION: /note="PEPTIDE IS AMIDATED AT CARBOXY TERMINUS"

(x i) SEQUENCE DESCRIPTION: SEQ ID NO:20:

His Cys Lys Phe Trp Tyr
1               5

(2) INFORMATION FOR SEQ ID NO:21:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i x) FEATURE:
(A) NAME/KEY: Peptide
(B) LOCATION: 6
(D) OTHER INFORMATION: /note="PEPTIDE IS AMIDATED AT CARBOXY TERMINUS"

(x i) SEQUENCE DESCRIPTION: SEQ ID NO:21:

His Cys Lys Phe Trp Val
1               5

(2) INFORMATION FOR SEQ ID NO:22:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i x) FEATURE:
(A) NAME/KEY: Peptide
(B) LOCATION: 6
(D) OTHER INFORMATION: /note="PEPTIDE IS AMIDATED IN CARBOXY TERMINUS"

(x i) SEQUENCE DESCRIPTION: SEQ ID NO:22:

Ala Cys Lys Phe Trp Trp
1               5

(2) INFORMATION FOR SEQ ID NO:23:

(i) SEQUENCE CHARACTERISTICS:
(A) LENGTH: 6 amino acids ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 6
                    ( D ) OTHER INFORMATION: /note="PEPTIDE IS AMIDATED IN
                        CARBOXY TERMINUS"

( x i ) SEQUENCE DESCRIPTION: SEQ ID NO:23:

His  Ala  Lys  Phe  Trp  Trp
    1                   5

( 2 ) INFORMATION FOR SEQ ID NO:24:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 6
                    ( D ) OTHER INFORMATION: /note="PEPTIDE IS AMIDATED IN
                        CARBOXY TERMINUS"

( x i ) SEQUENCE DESCRIPTION: SEQ ID NO:24:

His  Cys  Ala  Phe  Trp  Trp
    1                   5

( 2 ) INFORMATION FOR SEQ ID NO:25:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 6
                    ( D ) OTHER INFORMATION: /note="PEPTIDE IS AMIDATED AT
                        CARBOXY TERMINUS"

( x i ) SEQUENCE DESCRIPTION: SEQ ID NO:25:

His  Cys  Lys  Ala  Trp  Trp
    1                   5

( 2 ) INFORMATION FOR SEQ ID NO:26:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Peptide
                    ( B ) LOCATION: 6
                    ( D ) OTHER INFORMATION: /note="PEPTIDE IS AMIDATED AT
                        CARBOXY TERMINUS"

( x i ) SEQUENCE DESCRIPTION: SEQ ID NO:26:

```
His  Cys  Lys  Phe  Ala  Trp
1                    5
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6
        ( D ) OTHER INFORMATION: /note="PEPTIDE IS AMIDATED AT CARBOXY TERMINUS"

( x i ) SEQUENCE DESCRIPTION: SEQ ID NO:27:

```
His  Cys  Lys  Phe  Trp  Ala
1                    5
```

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
His  Cys  Lys  Phe  Trp  Trp
1                    5
```

VIRAL INTEGRASE INHIBITING PEPTIDES

BACKGROUND OF THE INVENTION

1. Field of the Invention

This invention relates generally to the fields of virology and molecular medicine and more specifically to peptides that reduce or inhibit the activity of a viral integrase.

2. Background Information

Infection with the human immunodeficiency virus (HIV) can cause a condition of severe immunosuppression known as acquired immunodeficiency syndrome (AIDS) in a subject. HIV infection has reached epidemic proportions and the number of infected individuals is continuing to increase worldwide. It is estimated that 2.5 million people are infected in the United States and that 20 to 40 million people are infected worldwide. There are approximately 500,000 reported AIDS cases in the U.S.

HIV infection is transmitted through sexual contact, exposure to infected blood through blood transfusion or the sharing of contaminated needles. In addition, infants can become infected in utero, during birth or from breast milk.

Currently, azidothymidine (AZT) and dideoxyinosine (ddI), which inhibits the virally encoded reverse transcriptase (RT), are the only licensed drugs available for treating HIV infection. Unfortunately, AZT and ddI therapy are limited by the ability of HIV to acquire resistance to killing by RT inhibitors. Furthermore, since patients must be maintained on such drugs for extended periods of time in order to control the virus, unacceptable toxic side effects can occur. For example, severe anemia and pancytopenia can occur with prolonged AZT therapy and diarrhea commonly occurs with ddI.

In order to avoid the limitations associated with AZT treatment, other reverse transcriptase inhibitors are currently being evaluated for efficacy in treating HIV infection. However, a suitable alternative agent that inhibits HIV infection while avoiding the complications associated with AZT treatment has not yet been identified. Thus, a need exists to identify agents that effectively reduce or inhibit HIV infection. The present invention satisfies this need and provides related advantages as well.

SUMMARY OF THE INVENTION

The present invention provides viral integrase inhibiting peptides having the amino acid sequence

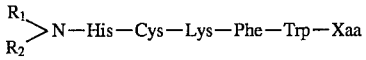  (SEQ ID NO: 1)

wherein Xaa is

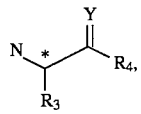

which is an amino acid or an amino acid analog that can have a chiral center. Each amino acid or amino acid analog present in a claimed viral integrase inhibiting peptide independently can be an L-amino acid or a D-amino acid and, if desired, the amino terminus or carboxy termini independently can be chemically modified. Thus, the invention provides, for example, a viral integrase inhibiting peptide having the amino acid sequence, His-Cys-Lys-Phe-Trp-Trp-NH$_2$ (SEQ ID NO: 19), where "NH$_2$" indicates the peptide is amidated at the C-terminus.

The invention also provides viral integrase inhibiting peptides having essentially the amino acid sequence

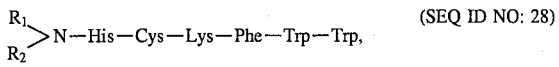 (SEQ ID NO: 28)

where a single amino acid such as alanine is substituted for one amino acid in SEQ ID NO: 28, any amino acid independently can be an L-amino acid or a D-amino acid and, if desired, the amino terminus or carboxy termini independently can be chemically modified. Thus, the invention provides, for example, a viral integrase inhibiting peptide having the amino acid sequence, His-Cys-Lys-Ala-Trp-Trp-NH$_2$ (SEQ ID NO: 25).

The invention also provides pharmaceutical compositions containing a viral integrase inhibiting peptide. In addition, the invention provides methods of using a viral integrase inhibiting peptide in vitro or in vivo to reduce or inhibit viral integrase activity, which can reduce or inhibit the infectivity of a virus.

DETAILED DESCRIPTION OF THE INVENTION

The present invention provides viral integrase inhibiting peptides having the amino acid sequence:

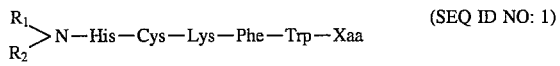 (SEQ ID NO: 1)

wherein Xaa is

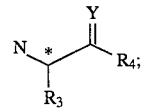

and wherein R$_1$ is H, COCH$_3$, CH$_2$Ph, CH$_2$CH$_2$Ph, COPh, COO-t-butyl, COOCH$_2$Ph or a linear or branched alkyl having 2 to 6 carbons; R$_2$ is H, C$_2$H$_5$ or CH$_2$Ph; R$_3$ is H, CH$_3$, CH$_2$—Ph, CH$_2$-pyridyl, CH$_2$-imidazole, CH$_2$-indole, CH$_2$—(CH$_2$)$_n$COOH, CH$_2$—(CH$_2$)$_n$CONHR$_5$, CH$_2$—(CH$_2$)$_n$NHR$_5$, CH$_2$—(CH$_2$)$_n$OH, CH$_2$—(CH$_2$)$_n$SR$_5$, or CH$_2$—(CH$_2$)$_n$NC(NH)NH$_2$; R$_4$ is OH, NH$_2$, SH, NHCH$_3$, N(CH$_3$)$_2$, NHCH$_2$Ph, or OR$_5$; and R$_5$ is H, CH$_3$, or a linear or branched alkyl having 2 to 6 carbons; and wherein Ph is C$_6$H$_5$, Y is O or H$_2$, n is 0, 1, 2 or 3 and, wherein when the carbon atom at "*" is a chiral center, the chiral center can be either R or S. As disclosed herein, the peptides of the invention can be further modified, for example, by acetylation of the amino terminus, by amidation of the carboxy terminus or by chemical modification of a reactive amino acid side group. For example, the invention provides a viral integrase inhibiting peptide having the amino acid sequence His-Cys-Lys-Phe-Trp-Trp-NH$_2$ (SEQ ID NO: 19), where "NH$_2$" indicates the peptide is amidated at the C-terminus (see, also, Table I, below). In addition, a particularly useful viral integrase inhibiting peptide of the invention can have H, C$_2$H$_5$ or CH$_2$Ph as R$_1$ and H or COCH$_3$ as R$_2$. Also, a particularly useful viral integrase inhibiting peptide of the invention can have the same moiety, which can be H, a linear alkyl having 2 to 6 carbons or a branched alkyl having 2 to 6 carbons, as both R$_1$ and R$_2$.

As used herein, the term "amino acid" is used generally to include naturally occurring proteogenic amino acids as well as non-naturally occurring amino acids such as D-amino acids and amino acid analogs, any of which can be incorporated into a peptide using the methods disclosed in Example I or otherwise known in the art. In view of this definition, one skilled in the art would know that reference herein to an amino acid, unless specifically indicated otherwise, includes, for example, naturally occurring proteogenic L-amino acids, D-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through well known metabolic pathways.

The invention also provides viral integrase inhibiting peptides having essentially the amino acid sequence

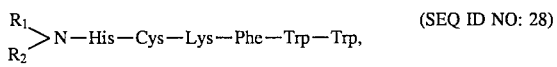 (SEQ ID NO: 28)

wherein $R_1$ is H, $COCH_3$, $CH_2Ph$, $CH_2CH_2Ph$, $COPh$, $COO$-t-butyl, $COOCH_2Ph$ or a linear or branched alkyl having 2 to 6 carbons; $R_2$ is H, $C_2H_5$ or $CH_2Ph$; and where any amino acid independently can be an L-amino acid or a D-amino acid and, if desired, the amino terminus or carboxy termini independently can be chemically modified. Thus, the invention provides, for example, a viral integrase inhibiting peptide having the amino acid sequence, His-Cys-Lys-Ala-Trp-Trp-$NH_2$ (SEQ ID NO: 25, see Table II, below). As used herein, the term "essentially the amino acid sequence" means a sequence such that shown as SEQ ID NO: 28, except having a single amino acid substitution as compared to SEQ ID NO: 28. For example, the peptide His-Cys-Lys-Ala-Trp-Trp-$NH_2$ (SEQ ID NO: 25), which has an alanine at amino acid position 4 as compared to a phenylalanine in SEQ ID NO: 28, is considered to have essentially the amino acid sequence of SEQ ID NO: 28.

A retrovirus such as HIV enters a mammalian cell via a surface receptor present on the cell. Upon entering the cell, the viral RNA is converted into a double stranded DNA molecule (proviral DNA) that integrates into the host cell genomic DNA. The proviral DNA encodes various gene products, including a reverse transcriptase and an integrase. Conversion of viral RNA into the proviral DNA requires the virally encoded reverse transcriptase and integration of the proviral DNA requires the virally encoded integrase enzyme. The viral integrase cleaves specific sequences in the proviral DNA, then effects integration of the proviral DNA into the host cell genome. The infected cell then becomes a source for the production of infectious retroviruses.

Nucleoside analogs such as AZT can inhibit the activity of the viral reverse transcriptase, thereby preventing the conversion of the viral RNA into a proviral DNA. As a result, the virus is not propagated and further infection by the virus is prevented. However, upon exposure to a nucleoside analog such as AZT, a retrovirus such as HIV can become resistant to the toxic effect of the drug. As a result, the usefulness of AZT treatment in an HIV infected individual is limited. Furthermore, the overall efficacy of AZT in preventing progression of AIDS or of a stage of the disease between HIV infection and the clinical appearance of AIDS, called AIDS-related complex (ARC), is in question.

The present invention provides effective viral integrase inhibiting peptides, which are hexapeptides containing L-amino acids, D-amino acids or amino acid analogs as disclosed herein. Examples of such viral integrase inhibiting peptides are shown in Tables I and II, where each amino acid is indicated by its three letter amino acid code, the stereochemistry is all L-amino acids and "$NH_2$" indicates the carboxy terminus of the peptide has been modified by amidation.

A viral integrase inhibiting peptide of the invention can reduce or inhibit the activity of a retroviral integrase such as the HIV integrase (Tables I and II), the simian immunodeficiency virus (SIV) integrase and the feline immunodeficiency virus (FIV) integrase (not shown). The hexapeptides of the invention were identified by screening a combinatorial peptide library for peptides that inhibited HIV integrase activity (see Example II). As disclosed herein, peptides having the general structure shown as SEQ ID NO: 1 or having essentially the amino acid sequence shown as SEQ ID NO: 28 can effectively inhibit HIV integrase activity (see Tables I and II, below). The skilled artisan will recognize that similar methods as disclosed in Example II can be used to identify a peptide that inhibits the activity of a viral integrase expressed, for example, by a retrovirus other than HIV, SIV or FIV, or by a transposable element such as a Ty element. For convenience of discussion, all such integrases, which are required for infectivity, are referred to generally as "viral" integrases.

In general, a useful viral inhibiting peptide of the invention will have viral integrase inhibiting activity within about two orders of magnitude of the activity of the peptide His-Cys-Lys-Phe-Trp-Trp-$NH_2$ (SEQ ID NO: 19). Thus, as disclosed herein, the peptides His-Cys-Lys-Phe-Trp-Arg-$NH_2$ (SEQ ID NO: 3); His-Cys-Lys-Phe-Trp-Gly-$NH_2$ (SEQ ID NO: 9); His-Cys-Lys-Phe-Trp-His-$NH_2$ (SEQ ID NO: 10); His-Cys-Lys-Phe-Trp-Ile-$NH_2$ (SEQ ID NO: 11); His-Cys-Lys-Phe-Trp-Phe-$NH_2$ (SEQ ID NO: 15); His-Cys-Lys-Phe-Trp-Tyr-$NH_2$ (SEQ ID NO: 20); and His-Cys-Lys-Phe-Trp-Val-$NH_2$ (SEQ ID NO: 21) are particularly effective viral integrase inhibiting peptides (see Table I, below).

In addition, a useful viral integrase inhibiting peptide can have essentially the amino acid sequence shown as SEQ ID NO: 28. Thus, as disclosed herein, the peptides Ala-Cys-Lys-Phe-Trp-Trp-$NH_2$ (SEQ ID NO: 22); His-Ala-Lys-Phe-Trp-Trp-$NH_2$ (SEQ ID NO: 23); His-Cys-Ala-Phe-Trp-Trp-$NH_2$ (SEQ ID NO: 24); His-Cys-Lys-Ala-Trp-Trp-$NH_2$ (SEQ ID NO: 25); His-Cys-Lys-Phe-Ala-Trp-$NH_2$ (SEQ ID NO: 26); and His-Cys-Lys-Phe-Trp-Ala-$NH_2$ (SEQ ID NO: 27) are particularly effective viral integrase inhibiting peptides.

Antiviral peptides provide a preferred alternative to the drugs currently used for treating viral infection. For example, an antiviral peptide can be designed to interfere with a particular stage in the life cycle of a virus or to act at a metabolic step where resistance is less likely to develop. There are multiple targets where a peptide can interfere with the life cycle of a virus. For example, peptides can be designed to block a particular cellular receptor such as the CD4 receptor, which HIV uses to enter a cell (Lifson et al., *Science* 241:712–716 (1988)). Peptides also can be designed to block the action of an essential enzyme encoded by the virus. As disclosed herein, the present invention provides viral integrase inhibiting peptides that can reduce or inhibit the activity of a retroviral integrase, which is a viral enzyme that is essential for viral infectivity.

The use of peptides as therapeutic agents is particularly advantageous because peptides can be synthesized in large numbers at relatively low cost and they can be readily modified to exhibit diverse properties (see, for example, Rees et al., *Protein Engineering: A Practical Approach* (IRL Press 1992), which is incorporated herein by reference). Viral integrase inhibiting peptides were synthesized using a modification of the solid phase peptide synthesis method (Merrifield (*J. Am. Chem. Soc.*, 85:2149 (1964); Houghten, U.S. Pat. No. 4,631,211, issued Dec. 23, 1986, each of which is incorporated herein by reference) or can be synthesized using standard solution methods well known in the art (see, for example, Bodanszky, M., *Principles of Peptide Synthesis* 2nd ed. (Springer-Verlag, 1988 and 1993, suppl.), each of which is incorporated herein by reference). Peptides prepared by the method of Merrifield can be synthesized using an automated peptide synthesizer such as the Applied Biosystems 431A-01 Peptide Synthesizer (Mountain View, Calif.) or using a manual peptide synthesis method (Houghten, supra, 1986).

As disclosed herein, viral integrase inhibiting hexapeptides were identified by screening a combinatorial hexapeptide library (see Example II). In view of the disclosed methods, the skilled artisan would recognize that combinatorial libraries of peptides having more than six amino acids or less than six amino acids also can be screened to identify other peptides that inhibit HIV integrase activity. Furthermore, while the disclosed methods can be used to identify peptides that inhibit HIV integrase activity, the skilled artisan would know that similar methods can be used to identify peptides that inhibit the integrase activity, for example, of other retroviruses such as Moloney murine leukemia virus or of transposable elements that require the activity of an encoded integrase for infectivity.

The claimed viral integrase inhibiting peptides were synthesized using L-amino acids, the active groups of which were protected as required using, for example, a t-butyldicarbonate (t-BOC) group or a fluorenylmethoxy carbonyl (FMOC) group. Amino acids and amino acid analogs can be purchased commercially (Sigma Chemical Co., St. Louis, Mo.; Advanced Chemtec, Louisville, Ky.) or synthesized using methods known in the art. Peptides synthesized using the solid phase method can be attached to a variety of resins, including, for example, 4-methylbenzhydrylamine (MBHA), 4-(oxymethyl)-phenylacetamido methyl and 4-(hydroxymethyl)phenoxymethyl-copoly(styrene)-1% divinylbenzene (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

The choice of amino acids or amino acid analogs incorporated into a peptide will depend, in part, on the specific physical, chemical or biological characteristics required of the viral integrase inhibiting peptide. Such characteristics are determined by whether, for example, the peptide is to be used in vivo or in vitro, and, when used in vivo, by the route by which the viral integrase inhibiting peptide will be administered or the location in a subject to which it will be directed. For example, the viral integrase inhibiting peptides exemplified herein were synthesized using only L-amino acids. However, the skilled artisan would know that any or all of the amino acids in a peptide of the invention can be a naturally occurring L-amino acid, a non-naturally occurring D-amino acid or an amino acid analog, provided the peptide can reduce or inhibit viral integrase activity.

Although a viral integrase inhibiting peptide as exemplified herein contain L-amino acids, either L-amino acids or D-amino acids can be incorporated at one or more positions in a peptide of the invention. The choice of including an L-amino acid or a D-amino acid in a viral integrase inhibiting peptide of the invention depends, in part, on the desired characteristics of the viral integrase inhibiting peptide. For example, the incorporation of one or more D-amino acids can confer increased stability on the peptide in vitro or in vivo. The incorporation of one or more D-amino acids also can increase or decrease the viral integrase inhibiting activity of the peptide as determined, for example, using the HIV integration assay (see Example II) or other well known methods for determining viral integrase activity in vitro or in vivo. Furthermore, since the viral integrase is required for viral infectivity, reduction or inhibition of viral integrase activity can reduce or inhibit viral infectivity. Thus, an assay measuring the infectivity of viruses exposed to a peptide of the invention can indicate indirectly the effectiveness of a viral integrase inhibiting peptide. Methods for determining the infectivity of various retroviruses are known in the art (see, for example, Hanson et al., *J. Clin. Microbiol.* 28:2030–2034 (1990), which is incorporated herein by reference).

In some cases, it can be desirable to allow a viral integrase inhibiting peptide to remain active for only a short period of time. In those cases, the incorporation of one or more L-amino acids in the peptide can allow, for example, endogenous peptidases in a subject to digest the peptide in vivo, thereby limiting the subject's exposure to an active viral integrase inhibiting peptide. The skilled artisan can determine the desirable characteristics required of a viral integrase inhibiting peptide by taking into consideration, for example, the age and general health of a subject, the extent of viral infection in the subject. The half life in a subject of a peptide having, for example, one or more D-amino acids substituted for a corresponding L-amino acid can be determined using methods well known to those in the field of pharmacology.

Selective modification of the reactive groups in a peptide also can impart desirable characteristics to a viral integrase inhibiting peptide. A peptide can be manipulated while still attached to the resin to obtain, for example, an N-terminal modified peptide such as an N-acetylated peptide. Alternatively, the peptide can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus and methods for amidation of the C-terminus (see Example I).

Similarly, methods for modifying the reactive side chain of an amino acid are well known in the art of peptide synthesis. For example, an amino acid side chain can be methylated, which can increase the uptake of a peptide by a cell (see, for example, Conradi et al., *Pharm. Res.* 9:435–439 (1992), which is incorporated herein by reference). The choice of modifications made to a reactive group present on a peptide of the invention will be determined, in part, by the characteristics required of the peptide. A newly synthesized peptide can be purified using a method such as reverse phase high performance liquid chromatography (RP-HPLC; see Example I) or other methods of separation based on the size or charge of the peptide. Similarly, well known methods such as amino acid sequence analysis or mass spectrometry (see Example I) can be used to characterize or confirm the structure of the viral integrase inhibiting peptide.

A viral integrase inhibiting peptide of the invention can be used in vitro, for example, to purge cells of a virus infection. For use in vitro, the peptide can be added directly to a solution such as tissue culture medium containing the cells or can be suspended in a suitable solution such as a buffer, which then can be contacted to the cells. The effectiveness of the viral integrase inhibiting peptide in reducing or preventing viral integrase activity can be determined using a viral integrase inhibition assay such as the assay disclosed in Example II or by examining the infectivity of the viruses present in the treated cells.

A viral integrase inhibiting peptide of the invention also can be used in vivo to treat a subject infected with a retrovirus such as HIV, SIV or FIV. Thus, the invention provides pharmaceutical compositions containing a viral integrase inhibiting peptide of the invention and a pharmaceutically acceptable carrier. Pharmaceutically acceptable carriers are well known in the art and include aqueous solutions such as physiologically buffered saline or other solvents or vehicles such as glycols, glycerol, vegetables oils (eg., olive oil) or injectable organic esters. A pharmaceutically acceptable carrier can be used to administer a viral integrase inhibiting peptide to a subject. A pharmaceutically acceptable carrier also can be useful for contacting a viral integrase inhibiting peptide with a cell in vitro.

A pharmaceutically acceptable carrier can contain physiologically acceptable compounds that act, for example, to stabilize the viral integrase inhibiting peptide or increase or decrease the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and sorbic acid.

The choice of a pharmaceutically acceptable carrier, including a physiologically acceptable compound, depends, for example, on the route of administration of the viral integrase inhibiting peptide and on the particular physicochemical characteristics of the specific viral integrase inhibiting peptide. For example, a physiologically acceptable compound such as aluminum monosterate or gelatin is particularly useful as a delaying agent, which prolongs the rate of absorption of a pharmaceutical composition administered to a subject by injection.

The invention further relates to methods of administering a pharmaceutical composition containing a viral integrase inhibiting peptide as claimed herein to a subject in order to reduce or inhibit the activity of a viral integrase in a virally infected cell. As used herein, the phrase "reduce or inhibit" means that the activity of viral integrase is decreased due to contact of the integrase with a viral integrase inhibiting peptide of the invention. The terms "reduce" and "inhibit" are used together because it is recognized that the activity of a viral integrase or infectivity of a virus can be reduced below the level detectable by a particular assay. As a result, it can be difficult to determine whether the activity or infectivity is completely inhibited or is reduced to undetectable level. Use of the phrase "reduce or inhibit" avoids the need to distinguish these events. It should be recognized, however, that while the terms "reduce" and "inhibit" generally are used together, the term "inhibiting" is used alone referring to a "viral integrase inhibiting peptide." In this case, the term "inhibiting" is used alone for convenience and is considered to mean "reduce or inhibit" as defined above.

As a result of the inhibition of viral integrase activity, viral infectivity can be reduced or inhibited. Thus, the invention provides a method for reducing or inhibiting the infectivity of a virus by contacting a cell containing the virus with a viral integrase inhibiting peptide of the invention. For example, the infectivity of a virus in a cell in culture can be reduced or inhibited by contacting the cell with a viral integrase inhibiting peptide of the invention. Similarly, the infectivity of a virus in a cell in a subject can be reduced or inhibited by administering a viral integrase inhibiting peptide of the invention to the subject.

The determination that the activity of a viral integrase is reduced or inhibited can be made, for example, using the HIV integrase inhibition assay as disclosed in Example II, which directly measures the effectiveness of a peptide of the invention to inhibit viral integrase activity. In addition, an indirect determination that the activity of a viral integrase is reduced or inhibited can be made by measuring the infectivity of a treated cell sample obtained, for example, from a virus-infected culture or from a patient. An indirect determination that the activity of a viral integrase is reduced or inhibited in vivo also can be made, for example, by performing a clinical examination such as observing a disappearance or decrease in the number of HIV infected T cells as compared to uninfected T cells. The skilled artisan would know other routine methods for determining whether a viral infection has been reduced or inhibited in vitro or in vivo due to administration of a viral integrase inhibiting agent.

A pharmaceutical composition containing a viral integrase inhibiting peptide of the invention can be administered to a subject by various routes, including orally, parenterally, intravenously, intramuscularly, subcutaneously, intraorbitally, intracapsularly, intraperitoneally, intracisternally, intravaginally, rectally or by passive or facilitated absorption through the skin using, for example, a skin patch or transdermal iontophoresis, respectively. The composition can be administered by bolus injection in a single dose, by multiple fractionated doses over a period of days or weeks or by continuous infusion. In addition, the composition can be administered over a sustained period of time, for example, using a dermal patch or an implant device such as a subdermal pump.

A pharmaceutical composition containing a viral integrase inhibiting peptide of the invention can be administered by injection, intubation or topically. Various methods of topical administration are useful and include, for example, passive topical administration such as by direct application of eye drops, an ointment or a powder or active topical administration such as by using a nasal spray or an inhalant. A pharmaceutical composition containing a viral integrase inhibiting peptide also can be administered as a topical spray, in which case one component of the composition can be an appropriate propellant.

The pharmaceutical composition also can be incorporated, if desired, into liposomes, microspheres or other polymer matrices (see, for example, Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer. Liposomes, for example, are particularly useful for administering a pharmaceutical composition containing a viral integrase inhibiting peptide to a cell in vitro in order to reduce or inhibit viral infection of the cells. Such a method can be useful, for example, where the cells are to be used for an autologous transplant. In this case, the cells are removed from the subject and contacted ex vivo with a peptide of the invention.

An effective amount of a viral integrase inhibiting peptide of the present invention can reduce or inhibit a viral infection of cells in culture. As used herein, an "effective amount" is a concentration of a viral integrase inhibiting peptide required to reduce or inhibit a viral infection in vitro. An effective amount of a viral integrase inhibiting peptide, which can be about 0.01 to about 100 mg/ml of medium, can be readily determined using, for example, the HIV integrase inhibition assay disclosed in Example II or other methods well known in the art.

As shown in Tables I and II, an effective amount of various viral integrase inhibiting peptides inhibited HIV integrase activity in vitro (see, also, Example II). In view of the results disclosed herein, the skilled artisan would recognize that an effective amount of a particular viral integrase inhibiting peptide can vary depending on several factors, including the activity of the viral integrase inhibiting peptide, other components, if any, present in a pharmacologically acceptable composition containing the peptide, and the physico-chemical properties of the peptide as discussed previously. The concentration of a viral integrase inhibiting peptide that is useful as an effective amount based on the methods described herein (see Example II) or otherwise well known in the art.

An effective amount of a viral integrase inhibiting peptide also can be used to reduce or inhibit a viral infection in a subject. As used herein, a "subject" means a mammal, including, for example, a human, a monkey or a cat. An effective amount of a viral integrase inhibiting peptide, which can be about 0.01 to about 100 mg/kg body weight, can be readily determined by considering the activity of the particular viral integrase inhibiting peptide being administered, the route of administration, the period over which the viral integrase inhibiting peptide is to be administered, the extent of viral infection and other factors known to those skilled in treating viral infections. Thus, the compounds described herein can be used as medicaments for the treatment of retroviral pathologies.

The following examples are intended to illustrate but not limit the present invention.

EXAMPLE I

Synthesis of A Viral Integrase Inhibiting Peptide Having the Amino Acid Sequence
His-Cys-Lys-Phe-Trp-Trp-NH$_2$ (SEQ ID NO: 19)

This example describes the method of solid phase peptide synthesis used to synthesize a viral integrase inhibiting peptide having the sequence shown above. Similar methods can be used to prepare any of the peptides of the invention.

MBHA resin containing t-BOC-formyl-Trp was added to a reaction vessel suitable for solid phase peptide synthesis using the "tea bag" method described by Houghten, supra, 1985. The resin was washed 3× with methylene chloride and the t-BOC protecting group was removed using trifluoroacetic acid (TFA) containing 1–2% anisole in methylene chloride.

Following removal of the protective group, the resin was washed with methylene chloride, then treated with diisopropylethylamine. The nascent peptide was extended by adding 3.2 equivalents of di-tolulyl-BOC-Trp in dimethylformamide (DMF) and 3.0 equivalents of dicyclohexylcarbodiimide in DMF to the reaction vessel. The reaction was allowed to proceed for 25 min and the extent of reaction was monitored using ninhydrin. Following the addition of each amino acid residue, the resin was washed with methylene chloride and the procedure was repeated using the appropriate protected amino acid derivatives (Advanced Chemtech; Louisville, Ky.). The N-formyl-BOC protecting group on the tryptophan residues was removed using 20% piperidine in DMF.

If desired, the hexapeptide can be acetylated at the amino terminus by treatment with acetic anhydride, then the peptide is washed with methylene chloride and cleaved from the resin using anhydrous hydrogen fluoride containing 10% anisole. The reaction mixture can be concentrated by evaporation and the residue digested with aqueous acetic acid. The acetic acid fraction, which contains the digested sample, is removed and the residue is washed with water. The wash can be added to the acetic acid fraction and the combined sample is concentrated.

The crude hexapeptide was purified by RP-HPLC (Vydac, C-18 column, using a gradient of 1 to 60% solution B over 30 min (solution A is 0.1% TFA/water and solution B is 0.1% TFA/acetonitrile). The peptide was determined to be greater than 90% pure by RP-HPLC (Vydac C-18 column, using a gradient of 5% to 55% solution B over 30 min; absorption was determined at 215 nm). The mass of the purified peptide was determined by mass spectrometry using a Kratos MALDITOF spectrometer. The mass of the peptide was measured and corresponded with the expected molecular mass.

EXAMPLE II

Identification of Peptides Having Viral Integrase Inhibiting Activity

This example describes methods for preparing and screening a combinatorial random peptide library to identify viral integrase inhibiting peptides.

A. Library preparation and screening:

A combinatorial random peptide library was constructed and screened for viral integrase inhibiting peptides using the HIV integrase inhibition assay described below. Briefly, random hexapeptides were synthesized using the "tea bag" using the method of Houghten, supra, 1986. Four hundred separate sample populations were prepared. The first and second positions (from the N-terminus) of the peptides in each sample was known and the remaining four positions in the population of peptides in each sample contained randomly incorporated amino acids.

The four hundred samples were screened for viral integrase inhibitory activity. The sample having His in position 1 and Cys in position 2 showed the greatest inhibitory activity. A second peptide library containing 20 sample populations was prepared. Each sample contained peptides having His and Cys in positions 1 and 2, respectively, a defined amino acid in position 3, and random amino acids in the remaining three positions. The 20 sample populations were screened to identify the population having the greatest ability to inhibit HIV integrase activity. The most active sample from the second screening contained Lys in position three.

The synthesis and screening steps were repeated, with a peptide having His, Cys and Lys in positions 1 to 3, respectively, a defined amino acid in position 4, and random amino acids in positions 5 and 6. Using this method, peptides having the sequence shown as SEQ ID NO: 1 were found to have significant HIV integrase inhibiting activity (see Table I, below).

Individual peptides within SEQ ID NO: 1 were prepared using the methods described in Example 1 and each was screened for HIV integrase inhibiting activity. As shown in Table I, various hexapeptides, including, for example, His-Cys-Lys-Phe-Trp-Trp-NH$_2$ (SEQ ID NO: 19); His-Cys-Lys-Phe-Trp-Arg-NH$_2$ (SEQ ID NO: 3); His-Cys-Lys-Phe-Trp-Gly-NH$_2$ (SEQ ID NO: 9); His-Cys-Lys-Phe-Trp-His-NH$_2$ (SEQ ID NO: 10); His-Cys-Lys-Phe-Trp-Ile-NH$_2$ (SEQ ID NO: 11); His-Cys-Lys-Phe-Trp-Phe-NH$_2$ (SEQ ID NO: 15); His-Cys-Lys-Phe-Trp-Tyr-NH$_2$ (SEQ ID NO: 20); and His-Cys-Lys-Phe-Trp-Val-NH$_2$ (SEQ ID NO: 21), when tested at a concentration of 50 μM, effectively inhibited HIV integrase activity. His-Cys-Lys-Phe-Trp-Trp-NH$_2$ (SEQ ID NO: 19) was particularly effective and was further modified as disclosed herein (see, also, Table II).

In some experiments, the amount of peptide included in the reaction was varied and the concentration of peptide that inhibited HIV integrase activity by 50% (IC-50) was determined. His-Cys-Lys-Phe-Trp-Trp-NH$_2$ (SEQ ID NO: 19; 2 μM); His-Cys-Lys-Phe-Trp-Ile-NH$_2$ (SEQ ID NO: 11; 4 μM); His-Cys-Lys-Phe-Trp-Arg-NH$_2$ (SEQ ID NO: 3; 8 μM); and His-Cys-Lys-Phe-Trp-Phe-NH$_2$ (SEQ ID NO: 15; 5 μM), for example, were particularly effective in reducing HIV integrase activity.

In order to determine the effectiveness of peptides having essentially the amino acid sequence of His-Cys-Lys-Phe-Trp-Trp-NH$_2$ (SEQ ID NO: 19), an alanine residue was substituted for each amino acid in SEQ ID NO: 19 and the HIV integrase inhibiting activity was examined. Six variants of the peptide of SEQ ID NO: 19 were synthesized, each variant having an alanine substitution at one of the six positions in the hexapeptide (see Table II), and the IC-50 was determined. As shown in Table II, the integrase inhibiting activity of each alanine substituted peptides was within about two orders of magnitude of the HIV

TABLE I

HIV INTEGRASE INHIBITION

| PEPTIDE* | SEQ ID NO: | % Inhibition** |
|---|---|---|
| His-Cys-Lys-Phe-Trp-Ala-NH$_2$ | 2 | 2 |
| His-Cys-Lys-Phe-Trp-Arg-NH$_2$ | 3 | 88 |
| His-Cys-Lys-Phe-Trp-Asn-NH$_2$ | 4 | 30 |
| His-Cys-Lys-Phe-Trp-Asp-NH$_2$ | 5 | 18 |
| His-Cys-Lys-Phe-Trp-Cys-NH$_2$ | 6 | 30 |
| His-Cys-Lys-Phe-Trp-Glu-NH$_2$ | 7 | 28 |
| His-Cys-Lys-Phe-Trp-Gln-NH$_2$ | 8 | 8 |
| His-Cys-Lys-Phe-Trp-Gly-NH$_2$ | 9 | 82 |
| His-Cys-Lys-Phe-Trp-His-NH$_2$ | 10 | 72 |
| His-Cys-Lys-Phe-Trp-Ile-NH$_2$ | 11 | 96 |
| His-Cys-Lys-Phe-Trp-Leu-NH$_2$ | 12 | 8 |
| His-Cys-Lys-Phe-Trp-Lys-NH$_2$ | 13 | 34 |
| His-Cys-Lys-Phe-Trp-Met-NH$_2$ | 14 | 42 |
| His-Cys-Lys-Phe-Trp-Phe-NH$_2$ | 15 | 95 |
| His-Cys-Lys-Phe-Trp-Pro-NH$_2$ | 16 | 45 |
| His-Cys-Lys-Phe-Trp-Ser-NH$_2$ | 17 | 40 |
| His-Cys-Lys-Phe-Trp-Thr-NH$_2$ | 18 | 8 |
| His-Cys-Lys-Phe-Trp-Trp-NH$_2$ | 19 | 100 |
| His-Cys-Lys-Phe-Trp-Tyr-NH$_2$ | 20 | 75 |
| His-Cys-Lys-Phe-Trp-Val-NH$_2$ | 21 | 85 |

*all peptides are written from N-terminus to C-terminus, left to right. The NH$_2$ shown at the right of a sequence indicates the C-terminus is amidated.
**HIV integrase assay was performed in the presence of 50 μM of the indicated peptide. Assay results were normalized to His-Cys-Lys-Phe-Trp-Trp-NH$_2$ (SEQ ID NO: 19) and are shown as the % inhibition of HIV integrase activity.

TABLE II

ALANINE SUBSTITUTED VIRAL INTEGRASE INHIBITING PEPTIDES

| PEPTIDE | SEQ ID NO: | IC-50* (μM) |
|---|---|---|
| His-Cys-Lys-Phe-Trp-Trp-NH$_2$ | 19 | 2 |

TABLE II-continued

ALANINE SUBSTITUTED VIRAL INTEGRASE INHIBITING PEPTIDES

| PEPTIDE | SEQ ID NO: | IC-50* (μM) |
|---|---|---|
| Ala-Cys-Lys-Phe-Trp-Trp-NH$_2$ | 22 | 51 |
| His-Ala-Lys-Phe-Trp-Trp-NH$_2$ | 23 | 30 |
| His-Cys-Ala-Phe-Trp-Trp-NH$_2$ | 24 | 49 |
| His-Cys-Lys-Ala-Trp-Trp-NH$_2$ | 25 | 8 |
| His-Cys-Lys-Phe-Ala-Trp-NH$_2$ | 26 | 150 |
| His-Cys-Lys-Phe-Trp-Ala-NH$_2$ | 27 | 210 |

*IC-50 is the concentration of the indicated peptide that reduces HIV integrase activity by 50%.

integrase inhibiting activity for His-Cys-Lys-Phe-Trp-Trp-NH$_2$ (SEQ ID NO: 19). His-Cys-Lys-Ala-Trp-Trp-NH$_2$ (SEQ ID NO: 25; 8 μM) was particularly effective at inhibiting HIV integrase activity.

B. HIV viral integrase assay:

HIV integrase activity was assayed by site-specific cleavage and integration of a 28 base pair synthetic oligonucleotide substrate representing HIV-1 U5 essentially as described by Vink et al., *Nucl. Acids Res.* 21:1419–1425 (1993), which is incorporated herein by reference. The HIV integrase used in these assays was expressed in *E. coli* and purified to near homogeneity.

Briefly, 0.2 pmol 5'-$^{32}$P-oligonucleotide substrate and 2 μM HIV integrase were incubated at 37° C. for 1 hr in 10 μl assay buffer (10 mM MOPS, pH 7.2, 50 mM NaCl, 3 mM MnCl$_2$, 0.05 mM EDTA, 0.1 mM β-mercaptoethanol, 4% glycerol). Control integrase activity was determined in the absence of any peptide. The activity of a peptide to be tested was examined by adding the peptide to the appropriate concentration in a 2 μl volume. Reactions were stopped by addition of 10 μl formamide loading dye (95% formamide, 20 mM EDTA, 0.05% bromophenol blue, 0.05% xylene cyanol) and incubation at 80° C. for 3 min. A 5 μl aliquot of the sample was separated by electrophoresis on a 12% denaturing polyacrylamide gel. Migration was detected by autoradiography and integrase activity was quantified by densitometry. Inhibition of integrase activity by a peptide corresponded with the disappearance of the cleavage and integration products.

Although the invention has been described with reference to the above-provided examples, it should be understood that various modifications can be made by those skilled in the art without departing from the invention. Accordingly, the invention is limited only by the following claims.

We claim:

1. A viral integrase inhibiting peptide having the amino acid sequence:

$$\begin{matrix}R_1\\R_2\end{matrix}\!\!>\!\!N-His-Cys-Lys-Phe-Trp-Xaa,$$ (SEQ ID NO: 1)

wherein Xaa is $$\underset{R_3}{\overset{Y}{N\!-\!\overset{*}{C}\!-\!R_1}};$$

wherein $R_1$ is H, $COCH_3$, $CH_2Ph$, $CH_2CH_2Ph$, $COPh$, COO-t-butyl, $COOCH_2Ph$, a linear alkyl having 2 to 6 carbons or a branched alkyl having 3 to 6 carbons, $R_2$ is H, $C_2H_5$, a linear alkyl having 2 to 6 carbons, a branched alkyl having 3 to 6 carbons, or $CH_2Ph$;

$R_3$ is H, $CH_3$, $CH_2$-Ph, $CH_2$-pyridyl, $CH_2$-imidazole, $CH_2$-indole, $CH_2$—$(CH_2)_n$COOH, $CH_2$—$(CH_2)_n$CONHR$_5$, $CH_2$—$(CH_2)_n$NHR$_5$, $CH_2$—$(CH_2)_n$SR$_5$, $CH_2$—$(CH_2)_n$NHC(NH)NH$_2$; or $CH_2$—$(CH_2)_n$OH;

$R_4$ is OH, $NH_2$, SH, $NHCH_3$, $N(CH_3)_2$, $NHCH_2Ph$, or $OR_5$; and $R_5$ is H, $CH_3$, a linear alkyl having 2 to 6 carbons or a branched alkyl having 3 to 6 carbons;

wherein Ph is $C_6H_5$, Y is O or $H_2$, n is 0, 1, 2 or 3; and, wherein when the carbon atom at "*" is a chiral center, the chiral center can be either R or S.

2. The viral integrase inhibiting peptide of claim 1, wherein the amino acids comprising said peptide are independently selected from the group consisting of D-amino acids and L-amino acids.

3. The viral integrase inhibiting peptide of claim 1, wherein the amino acids comprising said peptide are all L-amino acids.

4. The viral integrase inhibiting peptide of claim 1, wherein the amino terminus is modified.

5. The viral integrase inhibiting peptide of claim 4, wherein said modification is acetylation.

6. The viral integrase inhibiting peptide of claim 1, wherein the carboxy terminus is modified.

7. The viral integrase inhibiting peptide of claim 6, wherein said modification is amidation.

8. The viral integrase inhibiting peptide of claim 1, wherein both the amino terminus and the carboxy terminus are modified.

9. The viral integrase inhibiting peptide of claim 1, wherein $R_2$ is selected from the group consisting of H, $C_2H_5$ and $CH_2Ph$ and wherein $R_1$ is selected from the group consisting of H and $COCH_3$.

10. The viral integrase inhibiting peptide of claim 1, wherein $R_1$ is the same moiety as $R_2$ and wherein said same moiety is selected from the group consisting of H, a linear alkyl having 2 to 6 carbons and a branched alkyl having 3 to 6 carbons.

11. A viral integrase inhibiting peptide having essentially the amino acid sequence:

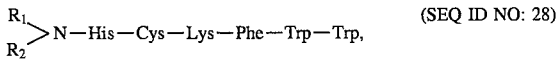   (SEQ ID NO: 28)

wherein $R_1$ is H, $COCH_3$, $CH_2Ph$, $CH_2CH_2Ph$, COPh, COO-t-butyl, $COOCH_2Ph$ or a linear alkyl having 2 to 6 carbons or a branched alkyl having 3 to 6 carbons; and $R_2$ is H, $C_2H_5$ or $CH_2Ph$.

12. The viral integrase inhibiting peptide of claim 11, wherein the amino acids comprising said peptide are independently selected from the group consisting of D-amino acids and L-amino acids.

13. The viral integrase inhibiting peptide of claim 11, wherein the amino acids comprising said peptide are all L-amino acids.

14. The viral integrase inhibiting peptide of claim 11, wherein the amino terminus is modified.

15. The viral integrase inhibiting peptide of claim 14, wherein said modification is acetylation.

16. The viral integrase inhibiting peptide of claim 11, wherein the carboxy terminus is modified.

17. The viral integrase inhibiting peptide of claim 16, wherein said modification is amidation.

18. The viral integrase inhibiting peptide of claim 11, wherein both the amino terminus and the carboxy terminus are modified.

19. A viral integrase inhibiting peptide, having the amino acid sequence:

His-Cys-Lys-Phe-Trp-Trp-$NH_2$ (SEQ ID NO: 19).

20. A viral integrase inhibiting peptide selected from the group consisting of:

His-Cys-Lys-Phe-Trp-Arg-$NH_2$ (SEQ ID NO: 3);
His-Cys-Lys-Phe-Trp-Gly-$NH_2$ (SEQ ID NO: 9);
His-Cys-Lys-Phe-Trp-His-$NH_2$ (SEQ ID NO: 10);
His-Cys-Lys-Phe-Trp-Ile-$NH_2$ (SEQ ID NO: 11);
His-Cys-Lys-Phe-Trp-Phe-$NH_2$ (SEQ ID NO: 15);
His-Cys-Lys-Phe-Trp-Tyr-$NH_2$ (SEQ ID NO: 20); and
His-Cys-Lys-Phe-Trp-Val-$NH_2$ (SEQ ID NO: 21).

21. A viral integrase inhibiting peptide having the amino acid sequence:

His-Cys-Lys-Ala-Trp-Trp-$NH_2$ (SEQ ID NO: 25).

22. A viral integrase inhibiting peptide selected from the group consisting of:

Ala-Cys-Lys-Phe-Trp-Trp-$NH_2$ (SEQ ID NO: 22);
His-Ala-Lys-Phe-Trp-Trp-$NH_2$ (SEQ ID NO: 23);
His-Cys-Ala-Phe-Trp-Trp-$NH_2$ (SEQ ID NO: 24);
His-Cys-Lys-Phe-Ala-Trp-$NH_2$ (SEQ ID NO: 26); and
His-Cys-Lys-Phe-Trp-Ala-$NH_2$ (SEQ ID NO: 27).

23. A composition of matter comprising a pharmaceutically acceptable carrier and a viral integrase inhibiting peptide, said peptide having the amino acid sequence:

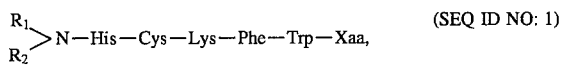   (SEQ ID NO: 1)

wherein Xaa is

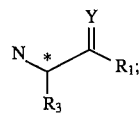

wherein $R_1$ is H, $COCH_3$, $CH_2Ph$, $CH_2CH_2Ph$, COPh, COO-t-butyl, $COOCH_2Ph$ or a linear alkyl having 2 to 6 carbons or a branched alkyl having 3 to 6 carbons;

R2 is H, $C_2H_5$, a linear alkyl having 2 to 6 carbons, a branched alkyl having 3 to 6 carbons, or $CH_2Ph$;

$R_3$ is H, $CH_3$, $CH_2$-Ph, $CH_2$-pyridyl, $CH_2$-imidazole, $CH_2$-indole, $CH_2$—$(CH_2)_n$COOH, $CH_2$—$(CH_2)_n$CONHR_5$, $CH_2$—$(CH_2)_n$NHR_5$, $CH_2$—$(CH_2)_n$SR_5$, $CH_2$—$(CH_2)_n$NHC(NH)NH_2$ or $CH_2$—$(CH_2)_n$OH$;

$R_4$ is OH, $NH_2$, SH, $NHCH_3$, $N(CH_3)_2$, $NHCH_2Ph$, or $OR_5$; and $R_5$ is H, $CH_3$, a linear alkyl having 2 to 6 carbons or a branched alkyl having 3 to 6 carbons;

and wherein Ph is $C_6H_5$, Y is O or $H_2$, n is 0, 1, 2 or 3; and, wherein when the carbon atom at "*" is a chiral center, the chiral center can be either R or S.

24. The composition of claim 23, wherein said peptide is His-Cys-Lys-Phe-Trp-Trp-$NH_2$ (SEQ ID NO: 19).

25. The composition of claim 23, wherein said peptide is selected from the group consisting of:

His-Cys-Lys-Phe-Trp-Arg-$NH_2$ (SEQ ID NO: 3);
His-Cys-Lys-Phe-Trp-Gly-$NH_2$ (SEQ ID NO: 9);
His-Cys-Lys-Phe-Trp-His-$NH_2$ (SEQ ID NO: 10);
His-Cys-Lys-Phe-Trp-Ile-$NH_2$ (SEQ ID NO: 11);
His-Cys-Lys-Phe-Trp-Phe-$NH_2$ (SEQ ID NO: 15);
His-Cys-Lys-Phe-Trp-Tyr-$NH_2$ (SEQ ID NO: 20); and
His-Cys-Lys-Phe-Trp-Val-$NH_2$ (SEQ ID NO: 21).

26. A composition of matter comprising a pharmaceutically acceptable carrier and a viral integrase inhibiting peptide, said peptide having essentially the amino acid sequence:

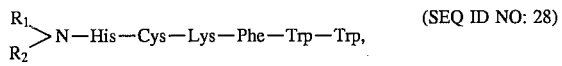   (SEQ ID NO: 28)

wherein $R_1$ is H, $COCH_3$, $CH_2Ph$, $CH_2CH_2Ph$, COPh, COO-t-butyl, $COOCH_2Ph$ a linear alkyl having 2 to 6 carbons or a branched alkyl having 3 to 6 carbons; and $R_2$ is H, $C_2H_5$ or $CH_2Ph$.

27. The composition of claim 26, wherein said peptide is His-Cys-Lys-Ala-Trp-Trp-$NH_2$ (SEQ ID NO: 25).

28. The composition of claim 26, wherein said peptide is selected from the group consisting of:

Ala-Cys-Lys-Phe-Trp-Trp-$NH_2$ (SEQ ID NO: 22);
His-Ala-Lys-Phe-Trp-Trp-$NH_2$ (SEQ ID NO: 23);
His-Cys-Ala-Phe-Trp-Trp-$NH_2$ (SEQ ID NO: 24);
His-Cys-Lys-Phe-Ala-Trp-$NH_2$ (SEQ ID NO: 26); and
His-Cys-Lys-Phe-Trp-Ala-$NH_2$ (SEQ ID NO: 27).

29. A method of reducing or inhibiting the activity of a viral integrase in a cell, comprising contacting the cell with an effective amount of the peptide of claim 1, said contacting reduces or inhibits the viral integrase activity.

30. The method of claim 29, wherein said contacting is in vitro.

31. The method of claim 29, wherein the viral integrase is a retrovirus gene product.

32. The method of claim 31, wherein said retrovirus is selected from the group consisting of human immunodeficiency virus, simian immunodeficiency virus and feline immunodeficiency virus.

33. A method of reducing or inhibiting the activity of a viral integrase in a cell, comprising contacting the cell with an effective amount of the peptide of claim 11, wherein said contacting reduces or inhibits the viral integrase activity.

34. The method of claim 33, wherein said contacting is in vitro.

35. The method of claim 33, wherein the viral integrase is a retrovirus gene product.

36. The method of claim 35, wherein said retrovirus is selected from the group consisting of human immunodeficiency virus, simian immunodeficiency virus and feline immunodeficiency virus.

37. A method of reducing or inhibiting the activity of a viral integrase in a cell in a subject, comprising administering to the subject an effective amount of the composition of claim 23.

38. The method of claim 37, wherein the viral integrase is a retrovirus gene product.

39. The method of claim 38, wherein said retrovirus is selected from the group consisting of human immunodeficiency virus, simian immunodeficiency virus and feline immunodeficiency virus.

40. A method of reducing or inhibiting the activity of a viral integrase in a cell in a subject, comprising administering to the subject an effective amount of the composition of claim 26.

41. The method of claim 40, wherein the viral integrase is a retrovirus gene product.

42. The method of claim 41, wherein said retrovirus is selected from the group consisting of human immunodeficiency virus, simian immunodeficiency virus and feline immunodeficiency virus.

* * * * *

UNITED STATES PATENT AND TRADEMARK OFFICE
CERTIFICATE OF CORRECTION

PATENT NO. : 5,578,573
DATED : November 26, 1996
INVENTOR(S) : Houghten et al.

Page 1 of 1

It is certified that error appears in the above-identified patent and that said Letters Patent is hereby corrected as shown below:

<u>Claim 1, column 27,</u>
Line 46, please delete "$R_1$" and replace therefor with -- $R_4$ --.

<u>Claim 23, column 29,</u>
Line 62, please delete "$R_1$" and replace therefor with -- $R_4$ --.

Signed and Sealed this

Eighteenth Day of September, 2001

*Attest:*

NICHOLAS P. GODICI
*Attesting Officer*   *Acting Director of the United States Patent and Trademark Office*